US012746109B2

(12) United States Patent
Ford

(10) Patent No.: US 12,746,109 B2
(45) Date of Patent: Sep. 29, 2026

(54) LYMPH CONDUCTION SYSTEM IMPLANT AND METHOD OF USING SAME

(71) Applicant: Bard Peripheral Vascular, Inc., Franklin Lakes, NJ (US)

(72) Inventor: Summer Ford, Queen Creek, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 865 days.

(21) Appl. No.: 18/002,713

(22) PCT Filed: Jun. 25, 2020

(86) PCT No.: PCT/US2020/039595
§ 371 (c)(1),
(2) Date: Dec. 21, 2022

(87) PCT Pub. No.: WO2021/262176
PCT Pub. Date: Dec. 30, 2021

(65) Prior Publication Data
US 2023/0240830 A1 Aug. 3, 2023

(51) Int. Cl.
*A61F 2/04* (2013.01)

(52) U.S. Cl.
CPC ........ *A61F 2/04* (2013.01); *A61F 2230/0006* (2013.01); *A61F 2250/0024* (2013.01);
(Continued)

(58) Field of Classification Search
CPC .................. A61F 2/04; A61F 2002/068; A61F 2250/0024; A61F 2002/018; A61F 2/2475; A61F 2/24; A61F 2/82
(Continued)

(56) References Cited

U.S. PATENT DOCUMENTS 6,689,150 B1 * 2/2004 VanTassel .......... A61B 17/0057 604/500
7,526,337 B2 4/2009 Shuros et al.
(Continued)

FOREIGN PATENT DOCUMENTS

CN 1399530 A 2/2003
CN 101896139 B 12/2012
(Continued)

OTHER PUBLICATIONS

Chinese Office Action for Appln. No. 202080102379.0 mailed Oct. 16, 2024, 20 pages.
(Continued)

*Primary Examiner* — Brian E Pellegrino
(74) *Attorney, Agent, or Firm* — Dinsmore & Shohl LLP

(57) ABSTRACT

A lymph conduction system implant includes a stent graft and a porous membrane. The stent graft has a non-porous tubular side wall. The non-porous tubular side wall has a proximal end and a distal end. The non-porous tubular side wall is configured to define a lumen having an inflow port at the proximal end and an outflow port at the distal end. All exposed surfaces of the stent graft are made of a first biocompatible material. The porous membrane is connected to the proximal end of the non-porous tubular side wall of the stent graft. The porous membrane is configured to span an entirety of a transverse area of the inflow port of the lumen of the stent graft. The porous membrane is made of a second biocompatible material.

3 Claims, 2 Drawing Sheets

(52) U.S. Cl.
CPC ................. *A61F 2250/0031* (2013.01); *A61F 2250/0067* (2013.01)

(58) Field of Classification Search
USPC .................................................. 623/1.24, 902
See application file for complete search history.

(56) References Cited

U.S. PATENT DOCUMENTS

| | | | |
|---|---|---|---|
| 7,894,906 | B2 | 2/2011 | Shuros |
| 8,126,538 | B2 | 2/2012 | Shuros et al. |
| 8,905,999 | B2 | 12/2014 | Shuros et al. |
| 9,061,094 | B2 | 6/2015 | Hyde et al. |
| 9,504,810 | B2 | 11/2016 | Cheng |
| 9,642,991 | B2 | 5/2017 | Eversull et al. |
| 9,682,223 | B2 | 6/2017 | Callaghan et al. |
| 10,149,684 | B2 | 12/2018 | Nitzan et al. |
| 10,639,458 | B2 | 5/2020 | Itkin et al. |
| 2003/0109824 | A1 * | 6/2003 | Anderson ............... A61F 2/011 604/104 |
| 2004/0167613 | A1 | 8/2004 | Yodfat et al. |
| 2007/0055365 | A1 | 3/2007 | Greenberg et al. |
| 2008/0020011 | A1 | 1/2008 | Finkelstein et al. |
| 2008/0234556 | A1 | 9/2008 | Brooke et al. |
| 2011/0190867 | A1 | 8/2011 | Vonderwalde et al. |
| 2013/0144375 | A1 * | 6/2013 | Giasolli .................... A61F 2/82 623/1.16 |
| 2014/0114227 | A1 | 4/2014 | Zamarripa et al. |
| 2016/0256605 | A1 | 9/2016 | Hadamitzky et al. |
| 2016/0331378 | A1 | 11/2016 | Nitzan et al. |
| 2017/0197066 | A1 | 7/2017 | Itkin et al. |
| 2018/0200185 | A1 | 7/2018 | Labib et al. |
| 2020/0054867 | A1 | 2/2020 | Schwartz et al. |

FOREIGN PATENT DOCUMENTS

| | | | | |
|---|---|---|---|---|
| WO | 2006116636 | A1 | 11/2006 | |
| WO | 2015130184 | A1 | 9/2015 | |
| WO | 2017015571 | A1 | 1/2017 | |
| WO | WO-2017079691 | A1 * | 5/2017 | ............. A61L 31/10 |

OTHER PUBLICATIONS

International Search Report and Written Opinion dated Mar. 23, 2021, in International Application No. PCT/US2020/039595.

* cited by examiner

LYMPH CONDUCTION SYSTEM IMPLANT AND METHOD OF USING SAME

CROSS-REFERENCE TO RELATED APPLICATIONS

This application is a U.S. National Phase of International Application No. PCT/US2020/039595, entitled "Lymph Conduction System Implant and Method of Using Same" and filed Jun. 25, 2020, which is incorporated herein by reference in its entirety.

TECHNICAL FIELD

The present invention relates to a device for use in a lymphatic system of a patient, and, more particularly, to a lymph conduction system implant and method of using same.

BACKGROUND ART

As cancer metastasizes from the original tumor into surrounding tissue, cancerous cells often become trapped within the lymph nodes of the patient. As a result, a physician can dissect one or more lymph nodes to thereby provide a diagnostic benefit of understanding whether or not the cancer has metastasized from the surrounding tissue, and to what extent. However, there may be adverse effects associated with lymph node dissection including, but not limited to, leaving the patient with a predisposition for infection, lymphoedema, oedema or seroma.

What is needed in the art is a device that will help negate the adverse effects following lymph node dissection by helping to restore proper conduction of lymph fluid at the site of lymph node dissection.

SUMMARY OF INVENTION

The present invention provides a device that will help negate the adverse effects following lymph node dissection by helping to restore proper conduction of lymph fluid at the site of lymph node dissection.

The invention, in one form, is directed to a lymph conduction system implant that includes a stent graft and a porous membrane. The stent graft has a non-porous tubular side wall. The non-porous tubular side wall has a proximal end and a distal end. The non-porous tubular side wall is configured to define a lumen having an inflow port at the proximal end and an outflow port at the distal end. All exposed surfaces of the stent graft are made of a first biocompatible material. The porous membrane is connected to the proximal end of the non-porous tubular side wall of the stent graft. The porous membrane is configured to span an entirety of a transverse area of the inflow port of the lumen of the stent graft. The porous membrane is made of a second biocompatible material.

The invention, in another form, is directed to a lymph conduction system implant that includes a stent graft, a drug eluting porous membrane, and a drug. The stent graft has a non-porous tubular side wall. The non-porous tubular side wall has an inferior lymphangion region end and a superior lymphangion region end. The non-porous tubular side wall is configured to define a lumen having an inflow port at the inferior lymphangion region end and an outflow port at the superior lymphangion region end. All exposed surfaces of the stent graft are made of a first biocompatible material. A drug eluting porous membrane is connected to the inferior lymphangion region end of the non-porous tubular side wall of the stent graft. The drug eluting porous membrane is configured to span an entirety of a transverse area of the inflow port of the lumen of the stent graft. The drug eluting porous membrane is made of a second biocompatible material. The drug is carried by the drug eluting porous membrane.

An advantage of the present invention is that the lymph conduction system implant helps to negate the adverse effects following lymph node dissection by helping to restore proper conduction of lymph fluid at the site of lymph node dissection.

Another advantage is that the drug eluting porous membrane may provide localized and/or systemic drug delivery with sustained/prolonged release.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate at least one embodiment of the invention, and such exemplifications are not to be construed as limiting the scope of the invention in any manner.

DESCRIPTION OF EMBODIMENTS

Figure 1:
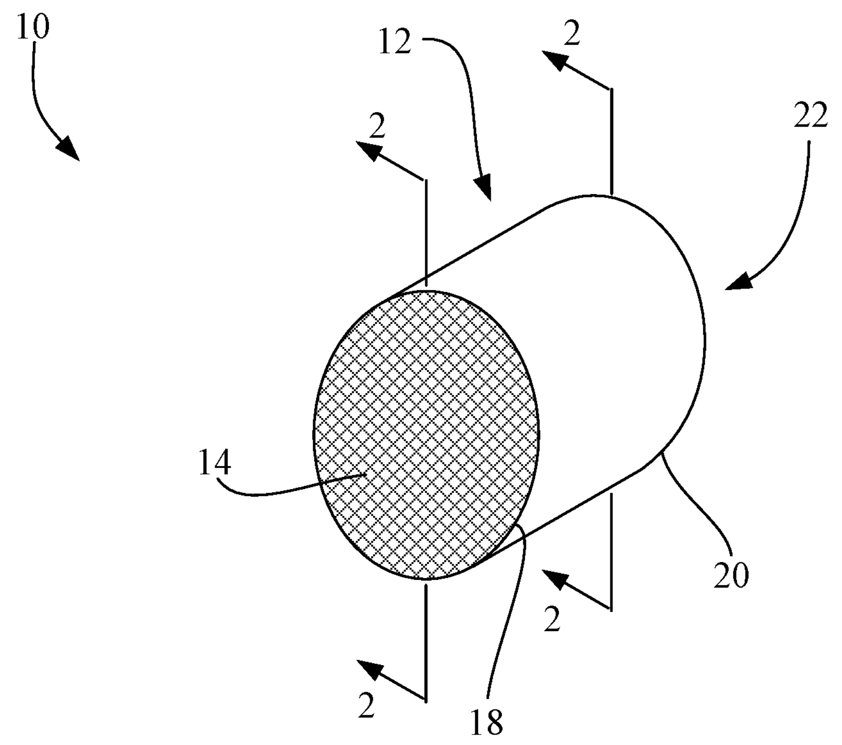
FIG. 1 is a perspective view of a lymph conduction system implant in accordance with an aspect of the present invention.
Figure 2:
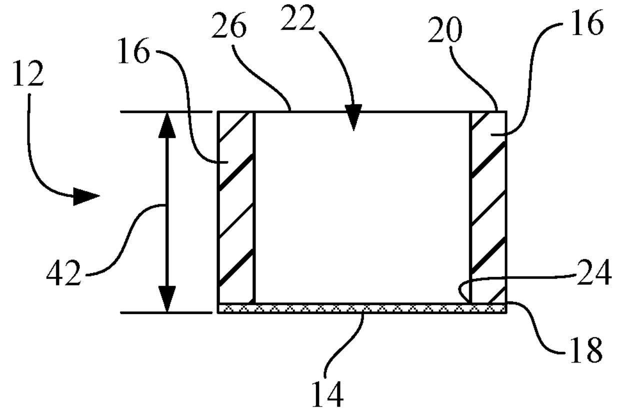
FIG. 2 is a section view of the lymph conduction system implant of FIG. 1 taken along plane 2-2-2-2 of FIG. 1.

Referring now to the drawings, and more particularly to FIGS. 1 and 2, there is shown a lymph conduction system implant 10 in accordance with an aspect of the present invention.

Lymph conduction system implant 10 includes a stent graft 12 and a porous membrane 14. Stent graft 12 has a non-porous tubular side wall 16. Non-porous tubular side wall 16 has a proximal end 18 and a distal end 20. Functionally, proximal end 18 also may be described herein as inferior lymphangion region end 18 of lymph conduction system implant 10, and distal end 20 also may be described herein as superior lymphangion region end 20 of lymph conduction system implant 10.

Non-porous tubular side wall 16 may be in the form of a polymer tubular member that defines a lumen 22 having an inflow port 24 at proximal end 18 and an outflow port 26 at distal end 20. The transverse cross-sectional shape of the polymer tubular member, and in turn lumen 22, may be, for example, circular or elliptical. Stent graft 12 may have a diameter that is an approximation of the diameter of the lymphatic vessel size into which lymph conduction system implant 10 is to be inserted, e.g., a diameter in a range of 0.2 millimeters (mm) to 2 mm, so as to provide a snug fit in the lymphatic vessel.

All exposed surfaces of stent graft 12 are made of a first biocompatible material, such as for example, expanded polytetrafluoroethylene (ePTFE). In the present embodiment, non-porous tubular side wall 16 includes ePTFE, such as for example, wherein non-porous tubular side wall 16 of stent graft 12 includes a coating of ePTFE. For example, the coating of ePTFE may be used to achieve the non-porosity of non-porous tubular side wall 16.

Porous membrane 14 may be connected, e.g., by ultrasonic or other weld, hot melt adhesive, or overmolding, to proximal end 18 of non-porous tubular side wall 16 of stent graft 12. Also, optionally, porous membrane 14 may be formed by direct electrospinning onto a surface of a polymer sheet, wherein the polymer sheet may be attached to stent graft 12 (e.g., via hot melt adhesive, direct wire attachment, or overmold) either before or after the electrospinning of porous membrane 14 onto the polymer sheet surface.

Porous membrane 14 is configured, in size and shape, to span an entirety of a transverse area of inflow port 24 of lumen 22 of stent graft 12. Porous membrane 14 may have a thickness, for example, in a range of 50 nanometers (nm) to 100 nm. Porous membrane 14 may be made of a second biocompatible material, and also may be made of a resorbable material. For example, the second biocompatible material of porous membrane 14 may include, in whole or in part, polyglycolide or polyglycolic acid (PGA) or polylactic-co-glycolic acid (PLGA). In the present embodiment, porous membrane 14 is a mesh of electrospun fibers that is coupled to proximal end 18 of non-porous tubular side wall 16 of stent graft 12, e.g., by one of the connection methods described above.

Optionally, porous membrane 14 may be configured as a drug eluting porous membrane that carries a drug. The drug may be, for example, an antibacterial drug, a chemo-therapeutic drug, and/or an anti-metastasis drug. The drug may be impregnated on and between the electrospun fibers making up porous membrane 14. Accordingly, for purposes of the drug eluting option, porous membrane 14 may sometimes also be referred to as drug eluting porous membrane 14.

Figure 3:
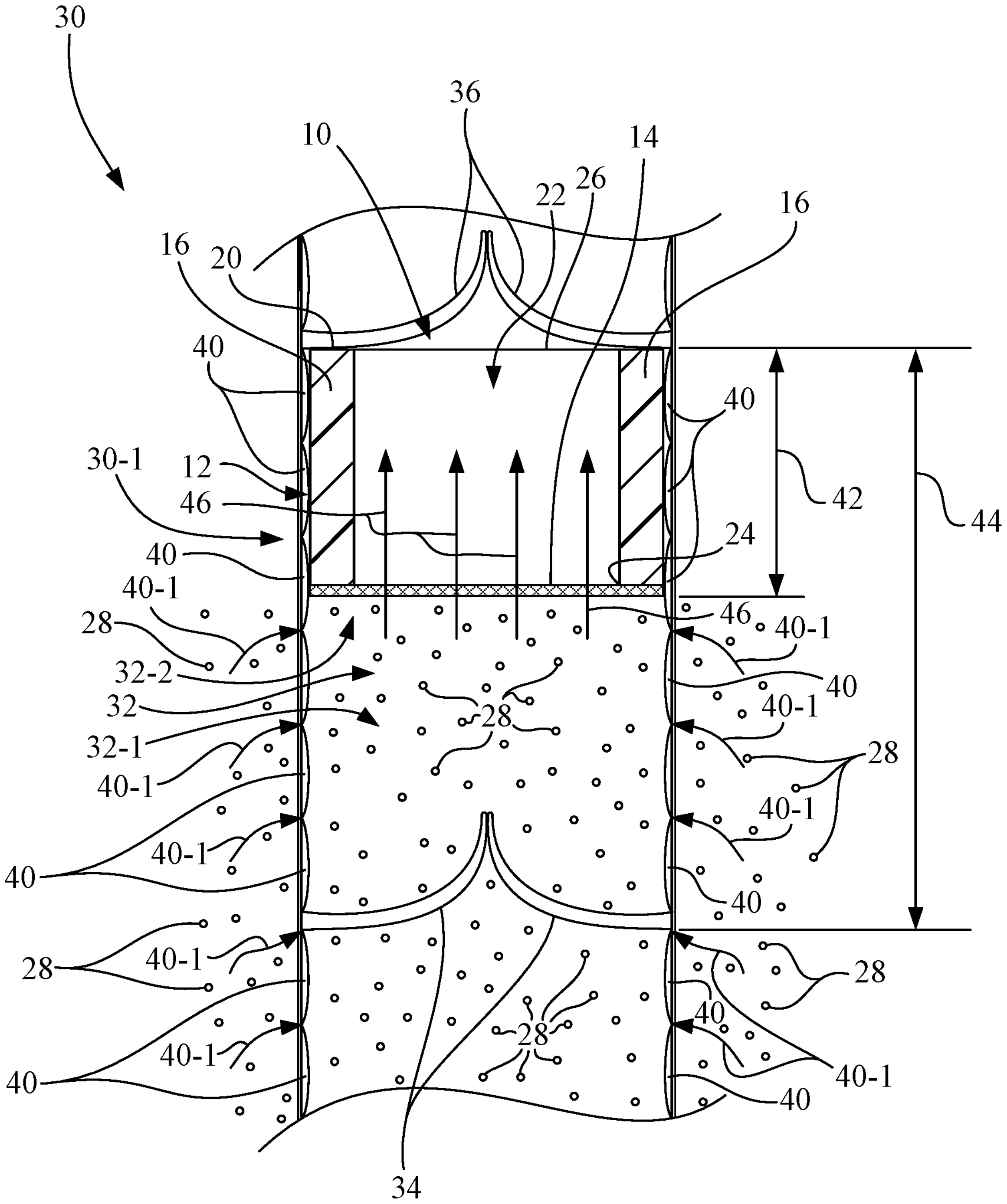
FIG. 3 is a pictorial illustration of the lymph conduction system implant of FIGS. 1 and 2 that is positioned in a lymphatic vessel of the lymphatic system in accordance with an aspect of the present invention.

Referring also to FIG. 3, lymph conduction system implant 10 is configured to facilitate conduction of lymph fluid 28 (represented in FIG. 3 as small circles) in a lymphatic vessel 30 following lymph node removal, or lymph node dissection, as a result of cancer metastasis or other causes. Lymph conduction system implant 10 may be deployed into the lymphatic system with a standard stent graft balloon system, placing lymph conduction system implant 10 at a site 30-1 of lymph node dissection. The method of use includes positioning lymph conduction system implant 10 in lymphatic vessel 30 in a lymphangion 32 between an inferior (entry) valve 34 in (i.e., at the proximal end of) an inferior lymphangion region 32-1 of lymphangion 32 and a superior (exit) valve 36 in (i.e., at a distal end of) a superior lymphangion region 32-2 of lymphangion 32. In the orientation of lymphangion 32 depicted in FIG. 3, inferior lymphangion region 32-1 may be considered to be the lower portion (e.g., lower half) of lymphangion 32 and superior lymphangion region 32-2 may be considered to be the upper portion (e.g., upper half) of lymphangion 32. Each of inferior (entry) valve 34 and superior (exit) valve 36 is a one-way bicuspid valve that prevents backwards drainage of lymph fluid 28.

The primary functionality of lymph conduction system implant 10 is that of restoring conduction of lymph fluid 28 to aid in preventing lymphoedema, seroma, or oedema following lymph node dissection. More particularly, distal end 20 (e.g., the open end) of stent graft 12 is positioned adjacent the superior (exit) valve 36 in superior lymphangion region 32-2 and proximal end 18 of stent graft 12 (e.g., the covered end) is positioned with porous membrane 14 facing the inferior (entry) valve 34 in inferior lymphangion region 32-1, so as to generate a pressure difference as well as a concentration gradient as an influx of lymph fluid 28 enters inferior lymphangion region 32-1 at a location proximal to lymph conduction system implant 10 through junctions 40-1 (represented by curved arrows) between endothelial cells 40 that are loosely layered and make up lymphatic vessel(s) 30, allowing flow of lymph fluid 28 into each lymphangion 32.

In the present embodiment, to facilitate conduction of lymph fluid 28, a length 42 of lymph conduction system implant 10 is no more than one-half of an overall length 44 of lymphangion 32. Stated differently, the length 42 of lymph conduction system implant 10 is no more than one-half of a distance (corresponding to overall length 44) between the inferior (entry) valve 34 in inferior lymphangion region 32-1 and the superior (exit) valve 36 in superior lymphangion region 32-2. For example, since an average length of lymphangion 32 may be approximately 2 mm, then the average length of stent graft 12 may be approximately less than or equal to 1 mm.

Accordingly, length 42 of lymph conduction system implant 10 is selected to allow for the superior region walls of superior lymphangion region 32-2 to be blocked off by non-porous tubular side wall 16 of stent graft 12 of lymph conduction system implant 10, while the inferior half (inferior lymphangion region 32-1) will remain uncovered, thereby allowing for natural influx of lymph fluid 28 into inferior lymphangion region 32-1 of lymphangion 32. This natural influx of lymph fluid 28 is enabled by the endothelium, a general term for the inner layer of a vessel, that is composed of an inner lining of single, flattened epithelial cells (simple squamous epithelium), i.e., endothelial cells 40. The endothelium has junctions 40-1 between endothelial cells 40 that allow interstitial lymph fluid 28 to flow into lymphatic vessel 30 when the pressure becomes high enough (such as from blood capillary hydrostatic pressure), but does not normally allow lymph fluid 28 to leak back out into the interstitial space. By blocking off superior lymphangion region 32-2 of lymphangion 32, and allowing inferior lymphangion region 32-1 of lymphangion 32 to remain unobstructed, a pressure difference, as well as a concentration gradient, will be created as an influx of lymph fluid 28 enters inferior lymphangion region 32-1 of lymphangion 32 through the junctions 40-1 between endothelial cells 40.

The natural conduction of lymph fluid 28 through lymphatic vessel(s) 30 result from the opening and closing of the one-way inferior (entry) valve 34 in inferior lymphangion region 32-1 and the superior (exit) valve 36 in superior lymphangion region 32-2 of lymphangion 32, wherein the opening and closing of the valves is induced primarily by smooth muscle contractions as well as secondary skeletal muscle contraction. This will additionally prevent lymph fluid 28 from flowing backwards. Once inferior (entry) valve 34 opens, lymph fluid 28 will flow into inferior lymphangion region 32-1, in addition to the lymph fluid 28 entering through the endothelial walls of lymphatic vessel 30. Once inferior lymphangion region 32-1 is saturated with lymph fluid 28, inferior (entry) valve 34 will be forced to close due to the fluid pressure distal to inferior (entry) valve 34.

Due to the inability of lymph fluid 28 to enter superior lymphangion region 32-2 through the endothelial walls of lymphatic vessel 30 due to obstruction by non-porous tubular side wall 16 of stent graft 12 of lymph conduction system implant 10, this blockage will create a negative pressure and/or a concentration gradient between inferior lymphangion region 32-1 and superior lymphangion region 32-2 of lymphangion 32. Due to this difference, lymph fluid 28 in inferior lymphangion region 32-1 will flow through porous membrane 14 through passive diffusion, represented by straight arrows 46, flowing into superior lymphangion region 32-2, creating an equilibrium within lymphangion 32. Once lymphangion 32 has met an equilibrium, pressure will begin to build as lymph fluid 28 is able to enter into inferior lymphangion region 32-1 as the junctions 40-1 between endothelial cells 40 are not blocked, allowing a pressure and/or concentration gradient to build up and continuously diffuse across porous membrane 14 until superior (exit) valve 36 gives way to the pressure and/or is opened via smooth muscle contraction. Once superior (exit) valve 36 opens, this allows for adequate conduction of lymph fluid 28 into the remaining lymphatic system and subsequent circulatory system.

The following items also relate to the invention.

In one embodiment, the invention relates to a lymph conduction system implant that includes a stent graft and a porous membrane. The stent graft has a non-porous tubular side wall. The non-porous tubular side wall has a proximal end and a distal end. The non-porous tubular side wall may be configured to define a lumen having an inflow port at the proximal end and an outflow port at the distal end. All exposed surfaces of the stent graft are made of a first biocompatible material. The porous membrane may be connected to the proximal end of the non-porous tubular side wall of the stent graft. The porous membrane may be configured to span an entirety of a transverse area of the inflow port of the lumen of the stent graft. The porous membrane may be made of a second biocompatible material, which may be different from the first biocompatible material.

In some embodiments, the second biocompatible material of the porous membrane may be a resorbable material.

In some embodiments, the second biocompatible material of the porous membrane may include PGA or PLGA.

In some embodiments, the porous membrane may be a mesh of electrospun fibers.

In some embodiments, the non-porous tubular side wall may include ePTFE.

In some embodiments, the non-porous tubular side wall may include a coating of ePTFE.

Optionally, the proximal end may be an inferior lymphangion region end. Optionally, the distal end may be a superior lymphangion region end. Optionally, a length of the lymph conduction system implant is no more than one-half of an overall length of a lymphangion. Optionally, a length of the lymph conduction system implant is no more than one-half of a distance between an entry valve in an inferior lymphangion region and the exit valve in the superior lymphangion region. Optionally, in some embodiments, the porous membrane may be a drug eluting porous membrane that carries a drug.

In embodiments having a drug, the drug may be an antibacterial drug, a chemo-therapeutic drug, and/or an anti-metastasis drug.

A method of using the lymph conduction system implant according to any one of the above-mentioned embodiments of paragraphs 0029-0036 may facilitate lymph fluid conduction in a lymphatic vessel following lymph node removal, and includes the step of positioning the lymph conduction system implant in the lymphatic vessel in a lymphangion between an entry valve in an inferior lymphangion region of the lymphangion and an exit valve in a superior lymphangion region of the lymphangion and, wherein the distal end of the stent graft may be positioned adjacent the exit valve in the superior lymphangion region and the proximal end of the stent graft may be positioned with the porous membrane facing the entry valve in the inferior lymphangion region, so as to generate a pressure difference as well as a concentration gradient as an influx of lymph fluid enters the inferior lymphangion region at a location proximal to the lymph conduction system implant through the junctions between endothelial cells of the lymphatic vessel.

In embodiments utilizing the method of using the lymph conduction system implant, a length of the lymph conduction system implant may be no more than one-half of an overall length of the lymphangion.

In embodiments utilizing the method of using the lymph conduction system implant, a length of the lymph conduction system implant may be no more than one-half of a distance between the entry valve in the inferior lymphangion region and the exit valve in the superior lymphangion region.

In any embodiment utilizing the method of using the lymph conduction system implant, the method may optionally include the further step of re-charging the porous membrane with an antibacterial drug, a chemo-therapeutic drug, and/or an anti-metastasis drug.

In another embodiment, the invention relates to a lymph conduction system implant having a stent graft, a drug eluting porous membrane, and a drug. The stent graft has a non-porous tubular side wall. The non-porous tubular side wall may have an inferior lymphangion region end and a superior lymphangion region end. The non-porous tubular side wall may be configured to define a lumen having an inflow port at the inferior lymphangion region end and an outflow port at the superior lymphangion region end. All exposed surfaces of the stent graft may be made of a first biocompatible material. The drug eluting porous membrane may be connected to the inferior lymphangion region end of the non-porous tubular side wall of the stent graft. The drug eluting porous membrane may be configured to span an entirety of a transverse area of the inflow port of the lumen of the stent graft. The drug eluting porous membrane may be made of a second biocompatible material, which may be different from the first biocompatible material. The drug may be carried by the drug eluting porous membrane.

In some embodiments, the second biocompatible material of the porous membrane may be a resorbable material that includes PGA or PLGA.

In some embodiments, the porous membrane may be a mesh of electrospun fibers.

In any embodiment having a drug, the drug may be an antibacterial drug, a chemo-therapeutic drug, and/or an anti-metastasis drug.

In some embodiments, the non-porous tubular side wall may include ePTFE.

In some embodiments, the non-porous tubular side wall may include a coating of ePTFE.

A method of using the lymph conduction system implant according to any one of the above-mentioned embodiments of paragraphs 0041-0046 may facilitate lymph fluid conduction in a lymphatic vessel following lymph node removal, and includes the step of positioning the lymph conduction system implant in the lymphatic vessel in a lymphangion between an entry valve in an inferior lymphangion region of the lymphangion and an exit valve in a superior lymphangion region of the lymphangion and, wherein the superior lymphangion region end of the stent graft may be positioned adjacent the exit valve in the superior lymphangion region and the inferior lymphangion region end of the stent graft may be positioned with the drug eluting porous membrane facing the entry valve in the inferior lymphangion region, so as to generate a pressure difference as well as a concentration gradient as an influx of lymph fluid enters the inferior lymphangion region at a location proximal to the lymph conduction system implant through the junctions between endothelial cells of the lymphatic vessel.

In the embodiment of paragraph 0047 utilizing the method of using the lymph conduction system implant, a length of the lymph conduction system implant may be no more than one-half of the overall length of the lymphangion.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of using a lymph conduction system implant, the method comprising:

positioning the lymph conduction system implant in a lymphatic vessel in a lymphangion between an entry valve in an inferior lymphangion region of the lymphangion and an exit valve in a superior lymphangion region of the lymphangion and, wherein a distal end of a stent graft of the lymph conduction system implant is positioned adjacent to the exit valve in the superior lymphangion region and a proximal end of the stent graft is positioned with a porous membrane thereof facing the entry valve in the inferior lymphangion region, so as to generate a pressure difference as well as a concentration gradient as an influx of lymph fluid enters the inferior lymphangion region at a location proximal to the lymph conduction system implant through junctions between endothelial cells of the lymphatic vessel, wherein a length of the lymph conduction system implant is no more than one-half of an overall length of the lymphangion.

2. The method of using the lymph conduction system implant according to claim 1, wherein the length of the lymph conduction system implant is no more than one-half of a distance between the entry valve in the inferior lymphangion region and the exit valve in the superior lymphangion region.

3. The method of using the lymph conduction system implant according to claim 1, further comprising:

impregnating the porous membrane with at least one of an antibacterial drug, a chemo-therapeutic drug, or an anti-metastasis drug.

* * * * *